United States Patent
Kimura et al.

(10) Patent No.: US 9,815,786 B2
(45) Date of Patent: Nov. 14, 2017

(54) METHOD FOR MANUFACTURING 3-(ALKYLSULFONYL)PYRIDINE-2-CARBOXYLIC ACID

(71) Applicant: SUMITOMO CHEMICAL COMPANY, LIMITED, Tokyo (JP)

(72) Inventors: Takahiro Kimura, Takarazuka (JP); Ryota Maehata, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/318,551

(22) PCT Filed: Jun. 22, 2015

(86) PCT No.: PCT/JP2015/067827
§ 371 (c)(1),
(2) Date: Dec. 13, 2016

(87) PCT Pub. No.: WO2015/199006
PCT Pub. Date: Dec. 30, 2015

(65) Prior Publication Data
US 2017/0129859 A1  May 11, 2017

(30) Foreign Application Priority Data
Jun. 26, 2014 (JP) ................. 2014-131041

(51) Int. Cl.
C07D 213/79 (2006.01)
C07D 213/83 (2006.01)
C07D 213/807 (2006.01)

(52) U.S. Cl.
CPC ....... *C07D 213/807* (2013.01); *C07D 213/79* (2013.01); *C07D 213/83* (2013.01)

(58) Field of Classification Search
None
See application file for complete search history.

(56) References Cited

U.S. PATENT DOCUMENTS 4,995,902 A * 2/1991 Brunner ............. A01N 43/40
                                              47/57.6
2009/0111791 A1   4/2009 De Lombaert et al.

FOREIGN PATENT DOCUMENTS

| CH | 657124 A5 | 8/1986 |
|---|---|---|
| WO | 2013/018928 A1 | 2/2013 |
| WO | 2014/104407 A1 | 7/2014 |

OTHER PUBLICATIONS

Blank et al., "Mercapto Heterocyclic Carboxylic Acids, Analogues of 3-Mercaptopicolinic Acid", Journal of Medicinal Chemistry, vol. 20, No. 4, 1977, pp. 572-576.

(Continued)

Primary Examiner — Zinna Northington Davis
(74) Attorney, Agent, or Firm — Birch, Stewart, Kolasch & Birch, LLP

(57) ABSTRACT

A compound represented by formula (7):

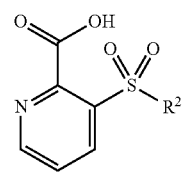

(7)

or a salt thereof can be manufactured by the following steps:

a step of allowing a compound represented by formula (1-S):

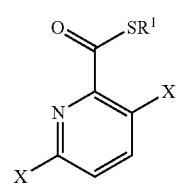

(1-S)

to react with a compound represented by formula (2):

$$R^2SM^2 \qquad (2)$$

to give a compound represented by formula (3-S):

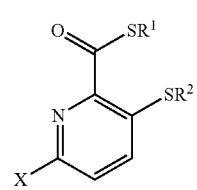

(3-S)

a step of allowing the compound represented by formula (3-S) to react with hydrogen peroxide in the presence of a tungsten catalyst and an acid to give a compound represented by formula (6-S) or a salt thereof:

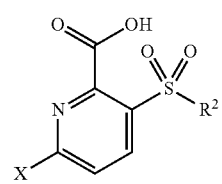

(6-S)

and
a step of reducing the compound represented by formula (6-S) or salt thereof in the presence of a base and a heterogeneous transition metal catalyst to give a compound represented by formula (7) or a salt thereof, wherein X, $R^1$, $R^2$, and $M^2$ are defined in the specification.

7 Claims, No Drawings

(56) References Cited

OTHER PUBLICATIONS

Blank et al., "Mercaptopyridinecarboxylic Acids, Synthesis and Hypoglycemic Activity", Journal of Medicinal Chemistry, vol. 17, No. 10, 1974, pp. 1065-1071.
International Preliminary Report on Patentability and Translation of the Written Opinion of the International Searching Authority (Forms PCT/IB/373 and PCT/ISA/237), dated Dec. 27, 2016, for International Application No. PCT/JP2015/067827.
International Search Report (Form PCT/ISA/210), dated Sep. 1, 2015, for International Application No. PCT/JP2015/067827, including an English translation.

* cited by examiner

METHOD FOR MANUFACTURING 3-(ALKYLSULFONYL)PYRIDINE-2-CARBOXYLIC ACID

TECHNICAL FIELD

The present invention relates to a method for producing a 3-(alkylsulfonyl)pyridine-2-carboxylic acid.

BACKGROUND ART

A 3-(alkylsulfonyl)pyridine-2-carboxylic acid is an important compound that serves as an intermediate in the production of pharmaceuticals and agrochemicals (e.g., WO 2013/018928), and various production methods are known.

Journal of Medicinal Chemistry, 1974, Vol. 17, No. 10, pp. 1065-1071, describes a method for producing 3-(methylthio)pyridine-2-carboxylic acid from 3-aminopicolinic acid, and Journal of Medicinal Chemistry, 1977, Vol. 20, No. 4, pp. 572-576, describes a method in which 3-(methylthio)pyridine-2-carboxylic acid is converted into a methyl ester, oxidized, and then hydrolyzed to produce 3-(methylsulfonyl)pyridine-2-carboxylic acid.

Meanwhile, for a method of producing a 3-(alkylthio)pyridine-2-carboxylic acid, a production method in which a 3-halogenopyridine-2-carboxylic acid is allowed to react with a thiol compound is known (WO 2013/018928).

SUMMARY OF INVENTION

The present invention provides a method for producing a 3-(alkylsulfonyl)pyridine-2-carboxylic acid compound from a 3,6-dihalogenopyridine-2-carboxylic acid.

According to the present invention, a compound represented by the below formula (7) or a salt thereof can be produced by a production method comprising:

Step AS of allowing a compound represented by formula (1-S):

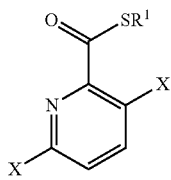
(1-S)

(wherein $R^1$ represents a $C_{1-8}$ straight-chain alkyl group, and X represents a halogen atom)
to react with a compound represented by formula (2):

$$R^2SM^2 \quad (2)$$

(wherein $R^2$ represents a $C_{1-8}$ straight-chain alkyl group, and $M^2$ represents a hydrogen atom or an alkali metal)
to give a compound represented by formula (3-S):

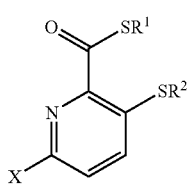
(3-S)

(wherein $R^1$, $R^2$, and X are as defined above);

Step CS of allowing the compound represented by formula (3-S) to react with hydrogen peroxide in the presence of a tungsten catalyst and an acid to give a compound represented by formula (6-S):

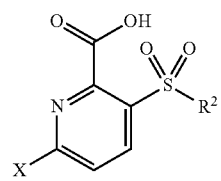
(6-S)

(wherein X and $R^2$ are as defined above); and

Step DS of allowing the compound represented by formula (6-S) or a salt thereof in the presence of a base and a heterogeneous transition metal catalyst to give a compound represented by formula (7) or a salt thereof:

(7)

(wherein $R^2$ is as defined above).

In addition, a compound represented by formula (7) or a salt thereof can also be produced by a production method comprising: Step BS of allowing a compound represented by formula (4):

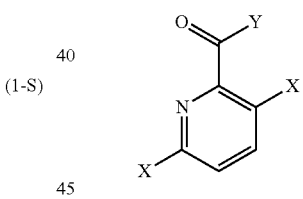
(4)

(wherein X represents a halogen atom, and Y represents a halogen atom)
to react with a compound represented by formula (5):

$$R^1SM^1 \quad (5)$$

(wherein $R^1$ represents a $C_{1-8}$ straight-chain alkyl group, and $M^1$ represents a hydrogen atom or an alkali metal)
to give a compound represented by formula (1-S); and
Step AS, Step CS, and Step DS mentioned above.

MODE FOR CARRYING OUT THE INVENTION

Hereinafter, the present invention will be described in detail.

$C_{1-8}$ straight-chain alkyl group is a methyl group, an ethyl group, a propyl group, a butyl group, an octyl group, or the like.

Halogen atom is a fluorine atom, a chlorine atom, a bromine atom, or an iodine atom.

Alkali metal means lithium, sodium, potassium, cesium, or the like.

In a compound represented by formula (1-S) (hereinafter referred to as compound (1-S)), $R^1$ is preferably a $C_{1-4}$ straight-chain alkyl group, and more preferably a methyl group or an ethyl group. Two Xs represent the same atoms, and are preferably chlorine atoms. Examples of compound (1-S) include S-methyl 3,6-dichloropyridine-2-thiocarboxylate, S-ethyl 3,6-dichloropyridine-2-thiocarboxylate, S-propyl 3,6-dichloropyridine-2-thiocarboxylate, S-butyl 3,6-dichloropyridine-2-thiocarboxylate, S-methyl 3,6-dibromopyridine-2-thiocarboxylate, S-ethyl 3,6-dibromopyridine-2-thiocarboxylate, S-propyl 3,6-dibromopyridine-2-thiocarboxylate, and S-butyl 3,6-dibromopyridine-2-thiocarboxylate.

In a compound represented by formula (2) (hereinafter referred to as compound (2)), $R^2$ is preferably a $C_{1-4}$ straight-chain alkyl group, and more preferably a methyl group or an ethyl group, and $M^2$ is preferably a hydrogen atom, sodium, or potassium. Examples of compound (2) include alkanethiols such as methanethiol, ethanethiol, propanethiol, butanethiol, and octanethiol; and alkali metal alkanethiolates such as lithium methanethiolate, sodium methanethiolate, potassium methanethiolate, lithium ethanethiolate, sodium ethanethiolate, potassium ethanethiolate, lithium propanethiolate, sodium propanethiolate, potassium propanethiolate, lithium butanethiolate, sodium butanethiolate, and potassium butanethiolate. Preferred are methanethiol, ethanethiol, sodium methanethiolate, potassium methanethiolate, sodium ethanethiolate, and potassium ethanethiolate.

Step AS is a step of allowing compound (1-S) to react with compound (2) to give a compound represented by formula (3-S) (hereinafter referred to as compound (3-S)).

In Step AS, in the case where compound (2) is an alkanethiol, such as methanethiol or ethanethiol, that is, in the case where compound (2) wherein $M^2$ is a hydrogen atom is used, the reaction is usually carried out in the presence of a base. Examples of the base include alkali metal hydrides such as lithium hydride, sodium hydride, and potassium hydride; alkali metal hydroxides such as lithium hydroxide, sodium hydroxide, and potassium hydroxide; alkaline earth metal hydroxides such as calcium hydroxide and barium hydroxide; and alkali metal alcoholates such as lithium methylate, sodium methylate, potassium methylate, lithium ethylate, sodium ethylate, potassium ethylate, lithium tert-butyrate, sodium tert-butyrate, and potassium tert-butyrate. Preferred are sodium hydride, potassium hydride, sodium hydroxide, potassium hydroxide, sodium methylate, potassium methylate, sodium ethylate, potassium ethylate, sodium tert-butyrate, and potassium tert-butyrate.

Step AS is usually performed in a solvent. Examples of the solvent include aromatic hydrocarbon solvents such as toluene, xylene, and ethylbenzene, halogenated aromatic hydrocarbon solvents such as monochlorobenzene and o-dichlorobenzene, ether solvents such as tetrahydrofuran and methyl tert-butyl ether, nitrile solvents such as acetonitrile and propionitrile, ester solvents such as ethyl acetate and propyl acetate, halogenated hydrocarbon solvents such as dichloromethane and 1,2-dichloroethane, amide solvents such as N,N-dimethylformamide, N,N-dimethylacetamide, and N-methylpyrrolidone, water, and mixed solvents thereof.

The reaction of compound (1-S) and compound (2) is usually carried out by mixing them. For mixing, compound (2) may be added to compound (1-S), or compound (1-S) may be added to compound (2).

In the case of using a base, compound (1-S) may be added to a mixture of compound (2) and a base, or a mixture of compound (2) and a base may be added to compound (1-S).

In addition, it is also possible to add a base to a mixture of compound (1-S) and compound (2).

The amount of compound (2) used is usually 0.8 to 3.0 times, preferably 1.0 to 1.5 times by mole of compound (1-S).

The amount of the base used is usually 0.8 to 3.0 times, preferably 0.9 to 1.2 times by mole of compound (2).

In the case where the reaction mixture separates into an organic layer and an aqueous layer, a phase transfer catalyst may be used. Examples of the phase transfer catalyst include quaternary ammonium salts such as tetrabutylammonium bromide, tetrabutylammonium chloride, tetrabutylammonium hydroxide, benzyltrimethylammonium bromide, benzyltrimethylammonium chloride, and benzyltrimethylammonium hydroxide; and phosphonium salts such as tetrabutylphosphonium chloride, tetrabutylphosphonium bromide, tetrabutylphosphonium hydroxide, tetraphenylphosphonium bromide, and tetraphenylphosphonium chloride.

The amount of the phase transfer catalyst used is usually 0.01 to 1.0 time, preferably 0.02 to 0.3 times by mole of compound (2).

The reaction temperature is usually −10 to 100° C., preferably 0 to 60° C. The reaction time depends on the reaction temperature, and is usually 1 to 50 hours.

After the completion of the reaction, compound (3-S) can be isolated by an ordinary work-up procedure. For example, water is added to the reaction mixture, followed by extraction with an organic solvent, and the obtained organic layer is concentrated, whereby compound (3-S) can be isolated. The obtained compound (3-S) may be further purified by column chromatography, recrystallization, or the like.

Typical examples of compound (3-S) include S-methyl 6-chloro-3-(methylthio)pyridine-2-thiocarboxylate, S-ethyl 6-chloro-3-(methylthio)pyridine-2-thiocarboxylate, S-propyl 6-chloro-3-(methylthio)pyridine-2-thiocarboxylate, S-butyl 6-chloro-3-(methylthio)pyridine-2-thiocarboxylate, S-methyl 6-bromo-3-(methylthio)pyridine-2-thiocarboxylate, S-ethyl 6-bromo-3-(methylthio)pyridine-2-thiocarboxylate, S-propyl 6-bromo-3-(methylthio)pyridine-2-thiocarboxylate, S-butyl 6-bromo-3-(methylthio)pyridine-2-thiocarboxylate, S-methyl 6-chloro-3-(ethylthio)pyridine-2-thiocarboxylate, S-ethyl 6-chloro-3-(ethylthio)pyridine-2-thiocarboxylate, S-propyl 6-chloro-3-(ethylthio)pyridine-2-thiocarboxylate, S-butyl 6-chloro-3-(ethylthio)pyridine-2-thiocarboxylate, S-methyl 6-bromo-3-(ethylthio)pyridine-2-thiocarboxylate, S-ethyl 6-bromo-3-(ethylthio)pyridine-2-thiocarboxylate, S-propyl 6-bromo-3-(ethylthio)pyridine-2-thiocarboxylate, S-butyl 6-bromo-3-(ethylthio)pyridine-2-thiocarboxylate, S-methyl 6-chloro-3-(propylthio)pyridine-2-thiocarboxylate, S-ethyl 6-chloro-3-(propylthio)pyridine-2-thiocarboxylate, S-propyl 6-chloro-3-(propylthio)pyridine-2-thiocarboxylate, S-butyl 6-chloro-3-(propyl)thiopyridine-2-thiocarboxylate, S-methyl 6-bromo-3-(propylthio)pyridine-2-thiocarboxylate, S-ethyl 6-bromo-3-(propylthio)pyridine-2-thiocarboxylate, S-propyl 6-bromo-3-(propylthio)pyridine-2-thiocarboxylate, S-butyl 6-bromo-3-(propylthio)pyridine-2-thiocarboxylate, S-methyl 6-chloro-3-(butylthio)pyridine-2-thiocarboxylate, S-ethyl 6-chloro-3-(butylthio)pyridine-2-thiocarboxylate, S-propyl 6-chloro-3-(butylthio)pyridine-2-thiocarboxylate, S-butyl 6-chloro-3-(butylthio)pyridine-2-thiocarboxylate, S-methyl 6-bromo-3-(butylthio)pyridine-2-thiocarboxylate, S-ethyl 6-bromo-3-(butylthio)pyridine-2-thiocarboxylate, S-propyl 6-bromo-3-(butylthio)pyridine-2-thiocarboxylate, and S-butyl 6-bromo-3-(butylthio)pyridine-2-thiocarboxylate.

Step CS is a step of allowing compound (3-S) to react with hydrogen peroxide in the presence of a tungsten catalyst and an acid to produce a compound represented by formula (6-S) (hereinafter referred to as compound (6-S)).

Hydrogen peroxide is usually used in the form of an aqueous solution, and the concentration is usually 10 to 70 wt %, preferably 30 to 60 wt %.

The amount of the hydrogen peroxide used is usually 3.0 to 10 times, preferably 4.0 to 8.0 times, and more preferably 5.0 to 6.0 times by mole of compound (3-S).

Examples of the tungsten catalyst include tungsten, tungstic acid, sodium tungstate, tungsten oxide, sodium phosphotungstate, and silicotungstic acid, and sodium tungstate is preferable.

The amount of the tungsten catalyst used is usually 0.5 to 10 mol, preferably 1.0 to 5.0 mol, per 100 mol of compound (3-S).

Examples of the acid include water-soluble acids such as sulfuric acid, methanesulfonic acid, ethanesulfonic acid, nitric acid, and phosphoric acid, and sulfuric acid is preferable.

The amount of the acid used is usually 0.01 to 1 time, preferably 0.05 to 0.2 times by mole of compound (3-S).

Step CS is usually performed in a solvent. For the solvent, water or a mixed solvent of water and an organic solvent is used. Examples of the organic solvent include aromatic hydrocarbon solvents such as toluene, xylene, and ethylbenzene; halogenated aromatic hydrocarbon solvents such as monochlorobenzene and o-dichlorobenzene; ether solvents such as tetrahydrofuran and methyl tert-butyl ether; nitrile solvents such as acetonitrile and propionitrile; ester solvents such as ethyl acetate and propyl acetate; halogenated hydrocarbon solvents such as dichloromethane and 1,2-dichloroethane; and amide solvents such as N, N-dimethylformamide, N, N-dimethylacetamide, and N-methylpyrrolidone.

Step CS is usually performed by mixing compound (3-S), hydrogen peroxide, a tungsten catalyst, and an acid. For a general mixing method, hydrogen peroxide is added to a mixture of compound (3-S), a tungsten catalyst, an acid, and water.

Step CS may also be performed in the presence of a sodium salt of ethylenediaminetetraacetic acid. The amount used is usually 0.8 to 1.5 times by mole of the tungsten catalyst.

The reaction temperature is usually 10 to 100° C., preferably 40 to 90° C. The reaction time depends on the reaction temperature, and is usually 1 to 50 hours.

After the completion of the reaction, excess hydrogen peroxide is removed, followed by extraction with an organic solvent, and the obtained organic layer is concentrated, whereby compound (6-S) can be obtained. In addition, by adding an alkali metal hydroxide, such as sodium hydroxide or potassium hydroxide, to compound (6-S), an alkali metal salt of compound (6-S) can be obtained. It is also possible that an aqueous solution of an alkali metal salt of compound (6-S) is suitably concentrated and cooled, thereby isolating an alkali metal salt of compound (6-S). Compound (6-S) or a salt thereof may also be further purified by recrystallization. It is also possible that an aqueous solution of an alkali metal salt of compound (6-S) and an acid, such as sulfuric acid or hydrochloric acid are mixed, and then the precipitated solid is collected by filtration, or alternatively the mixture is extracted with an organic solvent, and the organic layer is concentrated, thereby isolating compound (6-S).

Examples of compound (6-S) and a salt thereof include 6-chloro-3-(methylsulfonyl)pyridine-2-carboxylic acid, 6-bromo-3-(methylsulfonyl)pyridine-2-carboxylic acid, 6-chloro-3-(ethylsulfonyl)pyridine-2-carboxylic acid, 6-bromo-3-(ethylsulfonyl)pyridine-2-carboxylic acid, 6-chloro-3-(propylsulfonyl)pyridine-2-carboxylic acid, 6-bromo-3-(propylsulfonyl)pyridine-2-carboxylic acid, 6-chloro-3-(butylsulfonyl)pyridine-2-carboxylic acid, 6-bromo-3-(butylsulfonyl)pyridine-2-carboxylic acid, lithium 6-chloro-3-(methylsulfonyl)pyridine-2-carboxylate, lithium 6-bromo-3-(methylsulfonyl)pyridine-2-carboxylate, lithium 6-chloro-3-(ethylsulfonyl)pyridine-2-carboxylate, lithium 6-bromo-3-(ethylsulfonyl)pyridine-2-carboxylate, lithium 6-chloro-3-(propylsulfonyl)pyridine-2-carboxylate, lithium 6-bromo-3-(propylsulfonyl)pyridine-2-carboxylate, lithium 6-chloro-3-(butylsulfonyl)pyridine-2-carboxylate, lithium 6-bromo-3-(butylsulfonyl)pyridine-2-carboxylate, sodium 6-chloro-3-(methylsulfonyl)pyridine-2-carboxylate, sodium 6-bromo-3-(methylsulfonyl)pyridine-2-carboxylate, sodium 6-chloro-3-(ethylsulfonyl)pyridine-2-carboxylate, sodium 6-bromo-3-(ethylsulfonyl)pyridine-2-carboxylate, sodium 6-chloro-3-(propylsulfonyl)pyridine-2-carboxylate, sodium 6-bromo-3-(propylsulfonyl)pyridine-2-carboxylate, sodium 6-chloro-3-(butylsulfonyl)pyridine-2-carboxylate, sodium 6-bromo-3-(butylsulfonyl)pyridine-2-carboxylate, potassium 6-chloro-3-(methylsulfonyl)pyridine-2-carboxylate, potassium 6-bromo-3-(methylsulfonyl)pyridine-2-carboxylate, potassium 6-chloro-3-(ethylsulfonyl)pyridine-2-carboxylate, potassium 6-bromo-3-(ethylsulfonyl)pyridine-2-carboxylate, potassium 6-chloro-3-(propylsulfonyl)pyridine-2-carboxylate, potassium 6-bromo-3-(propylsulfonyl)pyridine-2-carboxylate, potassium 6-chloro-3-(butylsulfonyl)pyridine-2-carboxylate, and potassium 6-bromo-3-(butylsulfonyl)pyridine-2-carboxylate.

Step DS is a step of reducing compound (6-S) or a salt thereof in the presence of a base and a heterogeneous transition metal catalyst to give a compound represented by formula (7) (hereinafter referred to as compound (7)) or a salt thereof.

Examples of the heterogeneous transition metal catalyst include heterogeneous palladium catalysts such as palladium/carbon, palladium/silica, palladium/alumina, and palladium/barium sulfate; heterogeneous platinum catalysts such as platinum/carbon, platinum/silica, and platinum/alumina; heterogeneous ruthenium catalysts such as ruthenium/carbon, ruthenium/silica, and ruthenium/alumina; heterogeneous rhodium catalysts such as rhodium/carbon, rhodium/silica, and rhodium/alumina; heterogeneous iridium catalysts such as iridium/carbon; heterogeneous osmium catalysts such as osmium/carbon; heterogeneous nickel catalysts such as nickel-diatomaceous earth catalysts and Raney nickel; and cobalt catalysts such as Raney cobalt catalysts. Preferred are heterogeneous platinum-group catalysts including palladium, platinum, ruthenium, rhodium, iridium, and osmium, which are platinum-group elements. Heterogeneous palladium catalysts are more preferable for industrial use, and palladium/carbon is most preferable.

The amount of the heterogeneous catalyst used is usually 0.01 to 5 mol, preferably 0.05 to 0.5 mol, per 100 mol of compound (6-S).

The base may be any base capable of neutralizing the formed hydrogen halide. Examples thereof include alkali metal carbonates such as lithium carbonate, potassium carbonate, and sodium carbonate; alkali metal hydrogen carbonates such as lithium hydrogen carbonate, sodium hydrogen carbonate, and potassium hydrogen carbonate; alkali metal carboxylates such as lithium acetate, sodium acetate, potassium acetate, lithium oxalate, sodium oxalate, and potassium oxalate; alkali metal phosphates such as lithium phosphate, sodium phosphate, and potassium phosphate; alkali metal hydrogen phosphates such as lithium hydrogen phosphate, sodium hydrogen phosphate, and potassium hydrogen phosphate; and alkali metal dihydrogen phosphates such as lithium dihydrogen phosphate, sodium dihydrogen phosphate, and potassium dihydrogen phosphate.

The amount of the base used is usually 0.5 to 5.0 times, preferably 1.0 to 3.0 times by mole of compound (6-S). In the case where a salt of compound (6-S) is used, the amount of the base used is usually 0.3 to 3 times, preferably 0.5 to 1.5 times by mole of the salt of compound (6-S).

For the reduction reaction, a reducing agent such as hydrogen or ammonium formate is used.

In the case where hydrogen is used, the hydrogen partial pressure is usually 0.01 to 5 MPa, preferably 0.05 to 1 MPa.

In the case where ammonium formate is used, the amount used is usually 0.8 to 5 times, preferably 1.0 to 3.0 times by mole of compound (6-S).

The reduction reaction is usually carried out in a solvent. Examples of the solvent include water; alcohol solvents such as methanol, ethanol, and 2-propanol; aromatic hydrocarbon solvents such as toluene, xylene, and ethylbenzene; ether solvents such as tetrahydrofuran and methyl tert-butyl ether; ester solvents such as ethyl acetate and propyl acetate; ketone solvents such as acetone and methyl isobutyl ketone; amide solvents such as N,N-dimethylformamide, N,N-dimethylacetamide, and N-methylpyrrolidone; and mixed solvents thereof.

The reduction reaction in Step DS is usually carried out by mixing compound (6-S), a base, a heterogeneous transition metal catalyst, and a reducing agent. For a mixing method, for example, a reducing agent is added to a mixture of compound (6-S), a base, and a heterogeneous transition metal catalyst, or compound (6-S) and a reducing agent are each added to a mixture of a base and a heterogeneous transition metal catalyst.

The reaction temperature is usually 10 to 100° C., preferably 20 to 60° C. The reaction time depends on the reaction temperature and the hydrogen partial pressure, and is usually 1 to 50 hours.

After the completion of the reaction, the solids, including the catalyst, are removed by filtration, and the filtrate is concentrated, whereby a salt of compound (7) can be obtained.

An aqueous solution of an acid, such as hydrochloric acid or sulfuric acid, is added to the salt, and the precipitated solid is separated by filtration, or alternatively an aqueous solution of an acid, such as hydrochloric acid or sulfuric acid, is added to the salt, followed by extraction with an organic solvent, and the obtained organic layer is concentrated, whereby compound (7) can be isolated. Compound (7) or a salt thereof may also be further purified by recrystallization.

Typical examples of compound (7) and a salt thereof include 3-(methylsulfonyl)pyridine-2-carboxylic acid, 3-(ethylsulfonyl)pyridine-2-carboxylic acid, 3-(propylsulfonyl)pyridine-2-carboxylic acid, 3-(butylsulfonyl)pyridine-2-carboxylic acid, lithium 3-(methylsulfonyl)pyridine-2-carboxylate, lithium 3-(ethylsulfonyl)pyridine-2-carboxylate, lithium 3-(propylsulfonyl)pyridine-2-carboxylate, lithium 3-(butylsulfonyl)pyridine-2-carboxylate, sodium 3-(methylsulfonyl)pyridine-2-carboxylate, sodium 3-(ethylsulfonyl)pyridine-2-carboxylate, sodium 3-(propylsulfonyl)pyridine-2-carboxylate, sodium 3-(butylsulfonyl)pyridine-2-carboxylate, potassium 3-(methylsulfonyl)pyridine-2-carboxylate, potassium 3-(ethylsulfonyl)pyridine-2-carboxylate, potassium 3-(propylsulfonyl)pyridine-2-carboxylate, and potassium 3-(butylsulfonyl)pyridine-2-carboxylate.

Compound (1-S) can be produced by Step BS, in which a compound represented by formula (4) (hereinafter referred to as compound (4)) is allowed to react with a compound represented by formula (5) (hereinafter referred to as compound (5)).

In compound (4), X is preferably a chlorine atom, and Y is preferably a chlorine atom.

Examples of compound (4) include 3,6-difluoropyridine-2-carbonyl chloride, 3,6-difluoropyridine-2-carbonyl bromide, 3,6-difluoropyridine-2-carbonyl iodide, 3,6-dichloropyridine-2-carbonyl chloride, 3,6-dichloropyridine-2-carbonyl bromide, 3,6-dichloropyridine-2-carbonyl iodide, 3,6-dibromopyridine-2-carbonyl chloride, 3,6-dibromopyridine-2-carbonyl bromide, 3,6-dibromopyridine-2-carbonyl iodide, 3,6-diiodopyridine-2-carbonyl chloride, 3,6-diiodopyridine-2-carbonyl bromide, and 3,6-diiodopyridine-2-carbonyl iodide.

Compound (4) can be produced, for example, by halogenating the corresponding carboxylic acid with an acid halide or the like.

In compound (5), $R^1$ is preferably a $C_{1-8}$ straight-chain alkyl group, and more preferably a methyl group or an ethyl group, and M is preferably a hydrogen atom, sodium, or potassium.

Examples of compound (5) include alkanethiols such as methanethiol, ethanethiol, propanethiol, butanethiol, and octanethiol; and alkali metal alkanethiolates such as lithium methanethiolate, sodium methanethiolate, potassium methanethiolate, lithium ethanethiolate, sodium ethanethiolate, potassium ethanethiolate, lithium propanethiolate, sodium propanethiolate, potassium propanethiolate, lithium butanethiolate, sodium butanethiolate, and potassium butanethiolate. Preferred are methanethiol, ethanethiol, sodium methanethiolate, potassium methanethiolate, sodium ethanethiolate, and potassium ethanethiolate.

In the case where M in compound (5) is a hydrogen atom, Step BS may be performed in the presence of a base. Examples of the base include, in addition to the bases for use in Step AS, tertiary amines such as pyridine, triethylamine, and diisopropylethylamine.

Preferred examples of the base for use in Step BS include tertiary amines such as pyridine, triethylamine, and diisopropylethylamine; alkali metal hydrides such as sodium hydride and potassium hydride; alkali metal hydroxides such as sodium hydroxide and potassium hydroxide; and alkali metal tertiary alcoholates such as lithium tert-butyrate, sodium tert-butyrate, and potassium tert-butyrate.

Step BS is usually carried out in a solvent. Examples of the solvent include aromatic hydrocarbon solvents such as toluene, xylene, and ethylbenzene, halogenated aromatic hydrocarbon solvents such as monochlorobenzene and o-dichlorobenzene, ether solvents such as tetrahydrofuran and methyl tert-butyl ether, nitrile solvents such as acetonitrile and propionitrile, ester solvents such as ethyl acetate and propyl acetate, halogenated hydrocarbon solvents such as dichloromethane and 1,2-dichloroethane, amide solvents such as N,N-dimethylformamide, N,N-dimethylacetamide, and N-methylpyrrolidone, water, and mixed solvents thereof.

Step BS is usually performed by mixing compound (4) and compound (5). For mixing, compound (4) may be added to the compound (5), or compound (5) may be added to compound (4).

In the case of using a base, compound (4) may be added to a mixture of compound (5) and a base, or a mixture of compound (5) and a base may be added to compound (4). In addition, in the case where an alkali metal alcoholate is used, it is possible that a mixture of compound (5) wherein M is a hydrogen atom and an alkali metal alcoholate is concentrated and, after removing the by-product alcohol, allowed to react with compound (4).

In the case where the base is a tertiary amine, compound (5) may be added to a mixture of compound (4) and the base.

In the case where the reaction mixture separates into an organic layer and an aqueous layer, a phase transfer catalyst may be used. Examples of the phase transfer catalyst include quaternary ammonium salts such as tetrabutylammonium bromide, tetrabutylammonium chloride, tetrabutylammonium hydroxide, benzyltrimethylammonium bromide, benzyltrimethylammonium chloride, and benzyltrimethylammonium hydroxide; and phosphonium salts such as tetrabutylphosphonium chloride, tetrabutylphosphonium bromide, tetrabutylphosphonium hydroxide, tetraphenylphosphonium bromide, and tetraphenylphosphonium chloride.

The amount of the phase transfer catalyst used is usually 0.01 to 1.0 time, preferably 0.02 to 0.3 times by mole of compound (5).

The reaction temperature is usually −10 to 100° C., preferably 0 to 60° C. The reaction time depends on the reaction temperature, and is usually 1 to 50 hours.

The amount of compound (5) used is usually 0.8 to 3.0 times, preferably 1.0 to 1.5 times by mole of compound (4).

The amount of the base used is usually 0.8 to 3.0 times, preferably 0.9 to 1.2 times by mole of compound (5).

After the completion of the reaction, compound (1-S) can be isolated by an ordinary work-up procedure. For example, the reaction mixture is concentrated, or alternatively water is added to the reaction mixture, followed by extraction with an organic solvent, and the obtained organic layer is concentrated, whereby compound (1-S) can be isolated. The obtained compound (1-S) may be further purified by column chromatography or recrystallization.

In the case where compound (5) and compound (2) are the same, compound (3-S) can be obtained in one pot, without isolating the obtained compound (1-S) in the step BS.

In the case where M is a hydrogen atom in compound (2) and compound (5), for producing compound (3-S) in one pot, a base is usually used. The bases for use can be ones mentioned in Step AS. Preferred examples of the base for use in one-pot production include alkali metal hydrides such as sodium hydride and potassium hydride; alkali metal hydroxides such as sodium hydroxide and potassium hydroxide; and alkali metal tertiary alcoholates such as lithium tert-butyrate, sodium tert-butyrate, and potassium tert-butyrate.

The amount of compound (5) used is usually such that the total of compound (2) and compound (5) is 1.6 to 6 times, preferably 2.0 to 3.0 times, and more preferably 2.0 to 2.5 times by mole of compound (4).

The amount of the base used is usually 0.8 to 3.0 times, preferably 0.9 to 1.2 times by mole of compound (5).

In the case where the reaction mixture separates into an organic layer and an aqueous layer, a phase transfer catalyst may be used. Examples of the phase transfer catalyst include quaternary ammonium salts such as tetrabutylammonium bromide, tetrabutylammonium chloride, tetrabutylammonium hydroxide, benzyltrimethylammonium bromide, benzyltrimethylammonium chloride, and benzyltrimethylammonium hydroxide; and phosphonium salts such as tetrabutylphosphonium chloride, tetrabutylphosphonium bromide, tetrabutylphosphonium hydroxide, tetraphenylphosphonium bromide, and tetraphenylphosphonium chloride.

The amount of phase transfer catalyst used is usually 0.01 to 1.0 time, preferably 0.02 to 0.3 times by mole of compound (5).

The reaction temperature is usually −10 to 100° C., preferably 0 to 60° C. The reaction time depends on the reaction temperature, and is usually 1 to 50 hours.

After the completion of the reaction, compound (3-S) can be isolated by an ordinary work-up procedure. For example, water is added to the reaction mixture, followed by extraction with an organic solvent, and the obtained organic layer is concentrated, whereby compound (3-S) can be isolated. The obtained compound (3-S) may be further purified by column chromatography or recrystallization.

EXAMPLES

Hereinafter, the present invention will be described in detail with reference to examples. However, the present invention is not limited only to these examples.

First, production methods for compound (1-S) and compound (4) will be shown as reference examples.

Reference Example 1

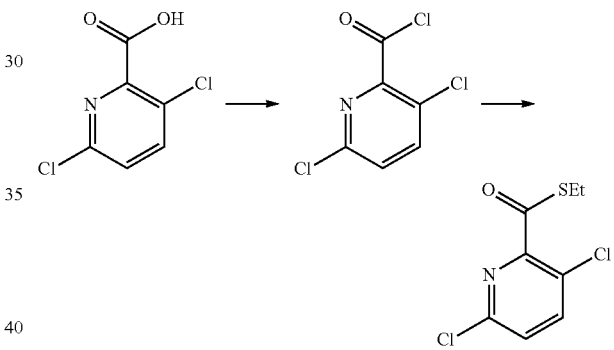

Under a nitrogen atmosphere, 34.08 g of thionyl chloride was added dropwise to a mixture of 52.63 g of 3,6-dichloropyridine-2-carboxylic acid (purity: 95.1 wt %), 100 g of toluene, and 0.95 g of N,N-dimethylformamide at 80° C. over 1 hour and stirred at the same temperature for 1 hour. The reaction mixture was cooled to 50° C. and concentrated to 82.17 g under reduced pressure. To the concentrate, 68 g of toluene was added, and 17.80 g of ethyl mercaptan was added dropwise at room temperature over 15 minutes and stirred at the same temperature for 1 hour. The reaction mixture was concentrated at 60° C. under reduced pressure, and 61.49 g of a toluene solution of S-ethyl 3,6-dichloropyridine-2-thiocarboxylate was obtained.

Reference Example 2

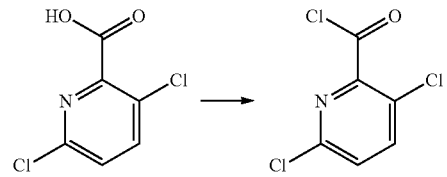 [SMILES: O=C(O)c1nc(Cl)ccc1Cl ; O=C(Cl)c1nc(Cl)ccc1Cl]

Under a nitrogen atmosphere, 17.04 g of thionyl chloride was added dropwise to a mixture of 26.29 g of 3,6-dichloropyridine-2-carboxylic acid (purity: 95.1 wt %), 63 g of toluene, and 0.48 g of N,N-dimethylformamide at 80° C. over 0.5 hours and stirred at the same temperature for 1.5 hours. The reaction mixture was cooled to 50° C. and concentrated under reduced pressure to give 47.67 g of a toluene solution of 3,6-dichloropyridine-2-carbonyl chloride (confirmed by mixing the reaction mixture with methanol).

Example 1

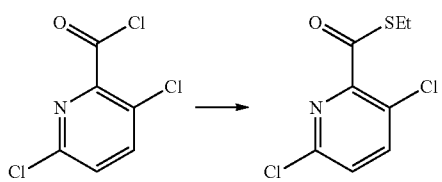

To 82.2 g of a toluene solution containing 54.8 g of 3,6-dichloropyridine-2-carbonyl chloride synthesized by the method described in Reference Example 2, 17.80 g of ethyl mercaptan was added dropwise at room temperature over 15 minutes and stirred at the same temperature for 1 hour. The reaction mixture was concentrated at 60° C. under reduced pressure to give 110.96 g of a toluene solution of S-ethyl 3,6-dichloropyridine-2-thiocarboxylate.

$^1$H-NMR (DMSO-$d_6$) δ: 1.25-1.29 (3H, t), 2.95-3.00 (2H, q), 7.84-7.88 (1H, d), 8.20-8.22 (1H, d)

Example 2

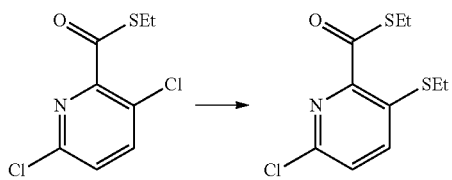

Under a nitrogen atmosphere, 5.79 g of ethyl mercaptan was added dropwise to a mixed solution of 3.92 g of sodium hydroxide (purity: 95%) and 20 g of water at room temperature over 2 minutes and stirred at the same temperature for 30 minutes. To the reaction mixture, 2.73 g of tetrabutylammonium bromide was added, and 36.09 g of the toluene solution of S-ethyl 3,6-dichloropyridine-2-thiocarboxylate synthesized in Reference Example 1 was added dropwise at 30° C. over 1 hour and stirred at the same temperature for 5 hours. After the layers were separated, the aqueous layer was removed, and the organic layer was washed with 10 g of 10 wt % aqueous sodium chloride solution. The organic layer was concentrated under reduced pressure to give 22.56 g of S-ethyl 6-chloro-3-(ethylthio)pyridine-2-thiocarboxylate (content: 85.85 wt %). The content of S-ethyl 3-chloro-6-(ethylthio)pyridine-2-thiocarboxylate was 4.3 wt %.

Example 3

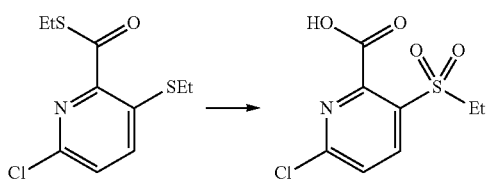

Aqueous hydrogen peroxide (31.3 wt %, 15.70 g) was added dropwise to a mixture of 10.0 g of S-ethyl 6-chloro-3-(ethylthio)pyridine-2-thiocarboxylate (purity: 80.2 wt %), 203.8 mg of sodium tungstate dihydrate, 227.5 mg of ethylenediaminetetraacetic acid disodium salt dihydrate, 241.1 mg of 96 wt % sulfuric acid, and 8 g of water at 80° C. over 6 hours. The reaction mixture was cooled to 50° C., and further 4.43 g of 31.3 wt % aqueous hydrogen peroxide was added dropwise over 1 hour and stirred at the same temperature for 2 hours. Subsequently, 1.53 g of sodium sulfite was added thereto in an ice bath, and an aqueous sodium hydroxide solution was added to adjust the pH of the reaction mixture 1.05, followed by extraction with methyl isobutyl ketone. An aqueous potassium hydroxide solution was added to the obtained organic layer to adjust the pH 5.6, and, after stirring at room temperature for 30 minutes, the layers were separated. To the obtained aqueous layer, 35 wt % hydrochloric acid was added to adjust the pH 0.8, and the precipitated solid was filtered. The solid was washed with water and dried, thereby giving 6.38 g 6-chloro-3-(ethylsulfonyl)pyridine-2-carboxylic acid.

$^1$H-NMR (CDCl3) δ: 8.47 (1H, d), 7.73 (1H, d), 3.70 (2H, q), 1.35 (3H, t)

Example 4

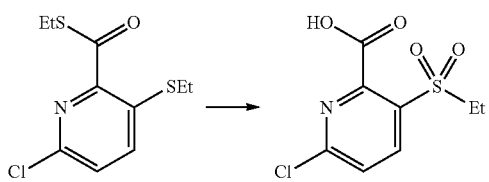

Aqueous hydrogen peroxide (18.26 g, 60.3 wt %) was added dropwise to a mixture of 20.00 g of S-ethyl 6-chloro-3-(ethylthio)pyridine-2-thiocarboxylate (purity: 96.00 wt %), 483.8 mg of sodium tungstate dihydrate, 505.2 mg of ethylenediaminetetraacetic acid disodium salt dihydrate, 568.0 mg of 96 wt % sulfuric acid, and 19.2 g of water at 80° C. over 8 hours. The reaction mixture was cooled to 50° C., and further 5.54 g of 60.3 wt % aqueous hydrogen peroxide was added dropwise over 1 hour and stirred at the same temperature for 8.5 hours. Subsequently, 1.77 g of a 20% aqueous sodium sulfite solution was added at room temperature, and an aqueous sodium hydroxide solution was added to adjust the pH of the reaction mixture 1.1, followed by extraction with methyl isobutyl ketone. The obtained organic layer was concentrated to 25.4 g, and 14.3 g of heptane was added dropwise at 60° C. The mixture was cooled and then stirred at room temperature for 3 hours, and the precipitated solid was filtered. The obtained solid was

Example 5

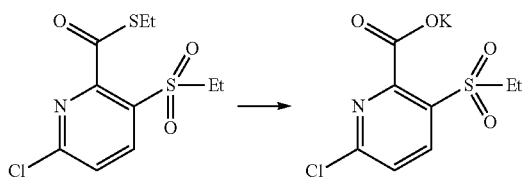

Aqueous hydrogen peroxide (125.6 g, 60.0 wt %) was added dropwise to a mixture of 111.69 g of S-ethyl 6-chloro-3-(ethylthio)pyridine-2-thiocarboxylate (purity: 89.53 wt %), 2.52 g of sodium tungstate dihydrate, 2.84 g of ethylenediaminetetraacetic acid disodium salt dihydrate, 3.06 g of 96 wt % sulfuric acid, 25.0 g of toluene, and 10.0 g of water at 50° C. over 8 hours and stirred at the same temperature for 1 hour. Subsequently, 33.1 g of a 22% aqueous sodium sulfite solution was added at room temperature, and a 48 wt % aqueous sodium hydroxide solution was added to adjust the pH of the reaction mixture 0.6, followed by extraction with methyl isobutyl ketone. An aqueous potassium hydroxide solution was added to the obtained organic layer to adjust the pH 5.5, and, after stirring at room temperature for 30 minutes, the layers are separated to give 260.4 g of an aqueous solution containing 96.4 g of potassium 6-chloro-3-(ethylsulfonyl)pyridine-2-carboxylate.

$^1$H-NMR (DMSO-$d_6$) δ: 1.05-1.09 (3H, t), 3.69-3.75 (2H, q), 7.51-7.53 (1H, d), 8.09-8.11 (1H, d)

Example 6

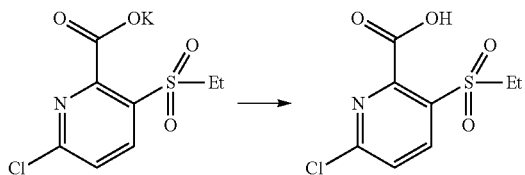

To a mixed solution of 24.4 g of 98% sulfuric acid and 70 g of water, 176.8 g of an aqueous solution containing 70.0 g of potassium 6-chloro-3-(ethylsulfonyl)pyridine-2-carboxylate was added dropwise at 10° C. over 2.5 hours. The mixture was heated to 40° C., stirred at the same temperature for 2 hours, and then cooled to 5° C., and the precipitated solid was filtered. The obtained solid was washed with 70 g of water and dried, thereby giving 58.1 g of 6-chloro-3-(ethylsulfonyl)pyridine-2-carboxylic acid.

Example 7

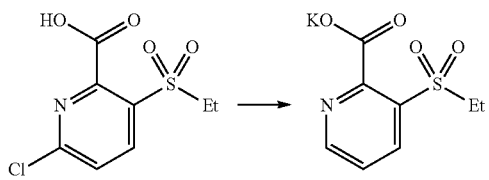

washed with 9.60 g of heptane and dried, thereby giving 16.70 g of 6-chloro-3-(ethylsulfonyl)pyridine-2-carboxylic acid.

Under a nitrogen atmosphere, 150 mg of Pd/C (Pd loading: 5 wt %, water content: 60.9 wt %) was added to a mixture of 3.00 g of 6-chloro-3-(ethylsulfonyl)pyridine-2-carboxylic acid, 6.00 g of methanol, and 2.53 g of potassium hydrogen carbonate and stirred at 40° C. for 6.5 hours under a hydrogen atmosphere. After purging with nitrogen, Pd/C was filtered, and Pd/C was washed with 6.34 g of methanol. The filtrate and the washing liquid were combined and concentrated to 6.48 g under reduced pressure. Subsequently, 6.00 g of toluene was added and concentrated to 7.24 g under reduced pressure. To the concentrate, 2.38 g of methanol was added, and concentrated to 8.21 g under reduced pressure. To the concentrate, 6.0 g of toluene was added and stirred at room temperature for 1 hour. The obtained solid was filtered, and the obtained solid was washed with 2.0 g of toluene and then dried under reduced pressure, thereby giving 2.66 g of potassium 3-(ethylsulfonyl)pyridine-2-carboxylate.

$^1$H-NMR (DMSO-$d_6$) δ: 1.03-1.07 (3H, t), 3.70-3.75 (2H, q), 7.38-7.41 (1H, m), 8.06-8.09 (1H, m), 8.61-8.64 (1H, m)

Example 8

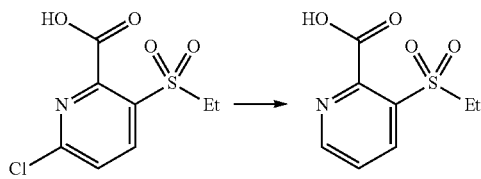 [SMILES: CCS(=O)(=O)c1ccc(Cl)nc1C(=O)O ; CCS(=O)(=O)c1cccnc1C(=O)O]

Under a nitrogen atmosphere, a mixed solution of 2.2 g of 6-chloro-3-(ethylsulfonyl)pyridine-2-carboxylic acid and 3.2 g of methanol was added to a mixture of 0.98 g of sodium carbonate and 1.6 g of methanol and stirred at room temperature for 10 minutes. To the mixture, 110 mg of Pd/C (Pd loading: 5 wt %, water content: 50 wt %) was added and stirred at 40° C. for 7 hours under a hydrogen atmosphere. Further, 110 mg of Pd/C was added and stirred at 40° C. for 4 hours under a hydrogen atmosphere. After purging with nitrogen, 2.2 g of water was added to the reaction mixture, Pd/C was filtered, and Pd/C was washed with 2.0 g of water. The filtrate and the washing liquid were combined and concentrated to 4.83 g under reduced pressure, and 0.90 g of 35 wt % hydrochloric acid was added dropwise over 1 hour and further stirred at room temperature for 1.5 hours. The obtained solid was filtered, and the obtained solid was washed with 1 g of water and then dried under reduced pressure, thereby giving 1.55 g of 3-(ethylsulfonyl)pyridine-2-carboxylic acid.

$^1$H-NMR (DMSO-$d_6$) δ: 1.15-1.19 (3H, t), 3.49-3.55 (2H, q), 7.79-7.83 (1H, m), 8.35-8.38 (1H, m), 8.90-8.92 (1H, m)

Example 9

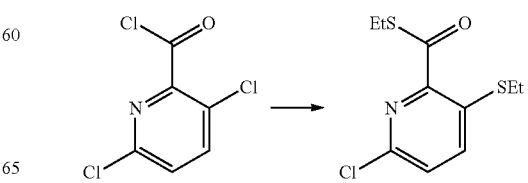

Under a nitrogen atmosphere, 3.40 g of ethyl mercaptan was added dropwise to a mixture of 2.17 g of sodium hydride (purity: 60.4 wt %) and 10 g of toluene at room temperature over 0.5 hours and stirred for 5 minutes. Subsequently, 9.80 g of the toluene solution of 3,6-dichloropyridine-2-carbonyl chloride obtained in Reference Example 2 below was added dropwise at 50° C. over 0.5 hours. The mixture was stirred at the same temperature for 3 hours and further stirred at room temperature for 16 hours. Subsequently, 0.24 g of ethyl mercaptan was added at 50° C. and stirred at the same temperature for 7 hours. The reaction mixture was washed with 10 g of water and then with 10 g of 10% aqueous sodium chloride solution, and the obtained organic layer was concentrated under reduced pressure, thereby giving 6.89 g of S-ethyl 6-chloro-3-(ethylthio)pyridine-2-thiocarboxylate (purity: 83.2 wt %). The content of S-ethyl 3-chloro-6-(ethylthio)pyridine-2-thiocarboxylate was 1.8 wt %.

$^1$H-NMR (DMSO-$d_6$) δ: 1.22-1.29 (6H, m), 2.89-2.94 (2H, q), 2.99-3.05 (2H, q), 7.72-7.74 (1H, m), 7.98-8.00 (1H, m)

Example 10

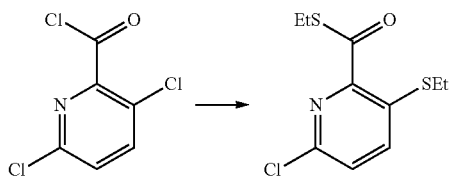

Under a nitrogen atmosphere, 6.80 g of ethyl mercaptan was added dropwise to a mixture of 1.68 g of tetrabutylammonium bromide, 4.60 g of sodium hydroxide (purity: 950), 10 g of water, and 10 g of toluene at room temperature over 10 minutes and stirred at the same temperature for 1 hour. To the reaction mixture, 20.00 g of a toluene solution of 3,6-dichloropyridine-2-carbonyl chloride (purity content: 10.96 g) was added dropwise at 20° C. over 30 minutes and stirred at the same temperature for 5 hours. The layers were separated, and the obtained organic layer was washed with 10 g of water and then concentrated under reduced pressure to give 13.59 g of S-ethyl 6-chloro-3-(ethylthio)pyridine-2-thiocarboxylate (content: 85.82 wt %). The content of S-ethyl 3-chloro-6-(ethylthio)pyridine-2-thiocarboxylate was 4.3 wt %, while the content of S-ethyl 3,6-di(ethylthio)pyridine-2-thiocarboxylate was 1.8 wt %.

Comparative Example 1

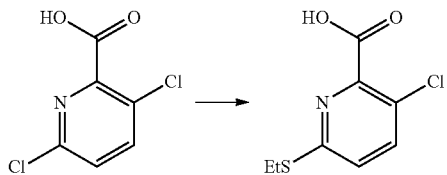

Under a nitrogen atmosphere, 35.5 mg of ethyl mercaptan was added to a mixture of 100 mg of 3,6-dichloropyridine-2-carboxylic acid, 45.7 mg of sodium hydride (content: 600), and 1 mL of tetrahydrofuran at room temperature and stirred at 40° C. for 2 hours. The reaction mixture was analyzed by liquid chromatography. As a result, 6-chloro-3-(ethylthio)pyridine-2-carboxylic acid was not formed, and 3-chloro-6-(ethylthio)pyridine-2-carboxylic acid was formed with an area percentage of 10%.

In the present invention, when a carboxylic acid (wherein $R^1$ is a hydrogen atom) was used in place of the ester wherein $R^1$ is a straight-chain alkyl group, it was not possible to selectively substitute the halogen atom at 3-position with an alkylthio group.

INDUSTRIAL APPLICABILITY

According to the method of the present invention, a compound useful as an intermediate in the production of pharmaceuticals and agrochemicals, such as 3-(alkylsulfonyl)pyridine-2-carboxylic acid, can be produced.

The invention claimed is:
1. A method for producing a compound represented by formula (7) or a salt thereof, comprising:
    a step of allowing a compound represented by formula (1-S):

(1-S)

wherein $R^1$ represents a $C_{1-8}$ straight-chain alkyl group, and X represents a halogen atom,
to react with a compound represented by formula (2):

$$R^2SM^2 \tag{2}$$

wherein $R^2$ represents a $C_{1-8}$ straight-chain alkyl group, and $M^2$ represents a hydrogen atom or an alkali metal,
to give a compound represented by formula (3-S):

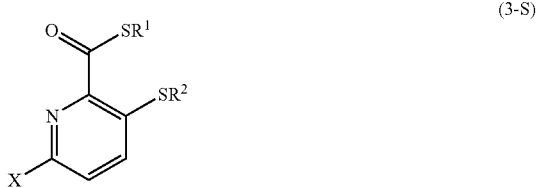

(3-S)

wherein $R^1$, $R^2$, and X are as defined above;
a step of allowing the compound represented by formula (3-S) to react with hydrogen peroxide in the presence of a tungsten catalyst and an acid to give a compound represented by formula (6-S) or a salt thereof:

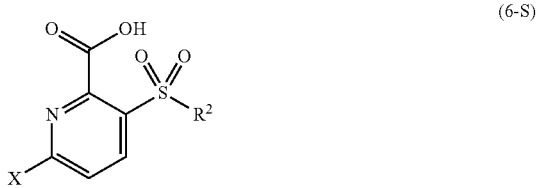

(6-S)

wherein X and $R^2$ are as defined above; and
a step of reducing the compound represented by formula (6-S) or salt thereof in the presence of a base and a heterogeneous transition metal catalyst to give a compound represented by formula (7) or a salt thereof:

(7)

wherein $R^2$ is as defined above.

2. A method for producing a compound represented by formula (7) or a salt thereof, comprising:

a step of allowing a compound represented by formula (4):

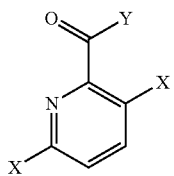

(4)

wherein X represents a halogen atom, and Y represents a halogen atom, to react with a compound represented by formula (5):

R¹SM¹  (5)

wherein $R^1$ represents a $C_{1-8}$ straight-chain alkyl group, and $M^1$ represents a hydrogen atom or an alkali metal, to give a compound represented by formula (1-S):

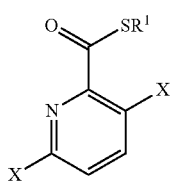

(1-S)

wherein $R^1$ and X are as defined above;

a step of allowing the compound represented by formula (1-S) to react with a compound represented by formula (2):

R²SM²  (2)

wherein $R^2$ represents a $C_{1-8}$ straight-chain alkyl group, and $M^2$ represents a hydrogen atom or an alkali metal, to give a compound represented by formula (3-S):

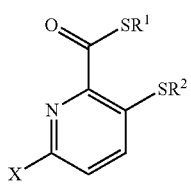

(3-S)

wherein $R^1$, $R^2$, and X are as defined above;

a step of allowing the compound represented by formula (3-S) to react with hydrogen peroxide in the presence of a tungsten catalyst and an acid to give a compound represented by formula (6-S):

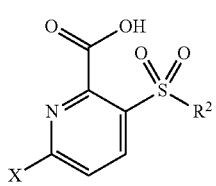

(6-S)

wherein X and $R^2$ are as defined above; and a step of reducing the compound represented by formula (6-S) or a salt thereof in the presence of a base and a heterogeneous transition metal catalyst to give a compound represented by formula (7) or a salt thereof:

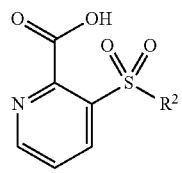

(7)

wherein $R^2$ is as defined above.

3. A method for producing a compound represented by formula (6-S) or a salt thereof, comprising:

a step of allowing a compound represented by formula (1-S):

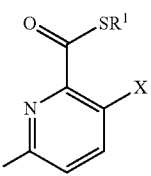

(1-S)

wherein $R^1$ represents a $C_{1-8}$ straight-chain alkyl group, and X represents a halogen atom, to react with a compound represented by formula (2):

R²SM²  (2)

wherein $R^2$ represents a $C_{1-8}$ straight-chain alkyl group, and $M^2$ represents a hydrogen atom or an alkali metal, to give a compound represented by formula (3-S):

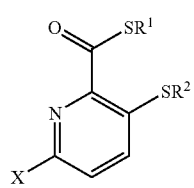

(3-S)

wherein $R^1$, $R^2$, and X are as defined above; and a step of allowing the compound represented by formula (3-S) to react with hydrogen peroxide in the presence of a tungsten catalyst and an acid to give a compound represented by formula (6-S) or a salt thereof:

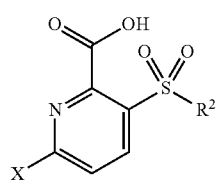

(6-S)

wherein X and $R^2$ are as defined above.

4. A method for producing a compound represented by formula (6-S) or a salt thereof, comprising:

a step of allowing a compound represented by formula (4):

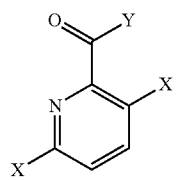

(4)

wherein X represents a halogen atom, and Y represents a halogen atom, to react with a compound represented by formula (5):

R¹SM¹ (5)

wherein R¹ represents a C$_{1-8}$ straight-chain alkyl group, and M¹ represents a hydrogen atom or an alkali metal, to give a compound represented by formula (1-S):

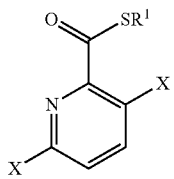
(1-S)

wherein R¹ and X are as defined above;
a step of allowing the compound represented by formula (1-S) to react with a compound represented by formula (2):

R²SM² (2)

wherein R² represents a C$_{1-8}$ straight-chain alkyl group, and M² represents a hydrogen atom or an alkali metal, to give a compound represented by formula (3-S):

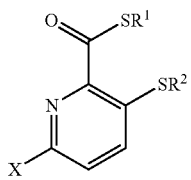
(3-S)

wherein R¹, R², and X are as defined above; and
a step of allowing the compound represented by formula (3-S) to react with hydrogen peroxide in the presence of a tungsten catalyst and an acid to give a compound represented by formula (6-S):

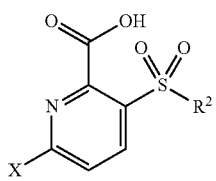
(6-S)

wherein X and R² are as defined above.

5. A method for producing a compound represented by formula (3-S), comprising allowing a compound represented by formula (1-S):

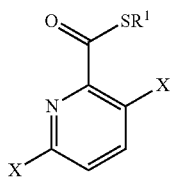
(1-S)

wherein R¹ represents a C$_{1-8}$ straight-chain alkyl group, and X represents a halogen atom, to react with a compound represented by formula (2):

R²SM² (2)

wherein R² represents a C$_{1-8}$ straight-chain alkyl group, and M² represents a hydrogen atom or an alkali metal, to give a compound represented by formula (3-S):

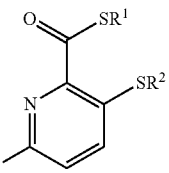
(3-S)

wherein R¹, R², and X are as defined above.

6. A method for producing a compound represented by formula (3-S), comprising:
a step of allowing a compound represented by formula (4):

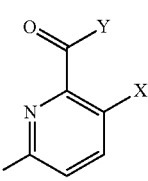
(4)

wherein X represents a halogen atom, and Y represents a halogen atom,
to react with a compound represented by formula (5):

R¹SM¹ (5)

wherein R¹ represents a C$_{1-8}$ straight-chain alkyl group, and M¹ represents a hydrogen atom or an alkali metal, to give a compound represented by formula (1-S):

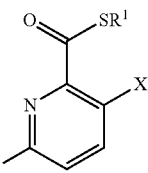
(1-S)

wherein R¹ and X are as defined above; and
a step of allowing the compound represented by formula (1-S) to react with a compound represented by formula (2):

R²SM² (2)

wherein R² represents a C$_{1-8}$ straight-chain alkyl group, and M² represents a hydrogen atom or an alkali metal, to give a compound represented by formula (3-S):

(3-S)

wherein R¹, R², and X are as defined above.

7. A compound represented by formula (3-S):
(3-S)
wherein $R^1$ represents a $C_{1-8}$ straight-chain alkyl group, $R^2$ represents a $C_{1-8}$ straight-chain alkyl group, and X represents a halogen atom.
* * * * *